United States Patent [19]

Bellas et al.

[11] Patent Number: 5,149,849
[45] Date of Patent: Sep. 22, 1992

[54] PROCESS FOR THE PREPARATION OF QUINHYDRONES

[75] Inventors: Michael Bellas, Yeong-Jen Kuo, both of Kingsport, Tenn.; Fred H. Rash, Kingsport, Tenn.

[73] Assignee: Eastman Kodak Company Rochester, New York

[21] Appl. No.: 670,661

[22] Filed: Mar. 18, 1991

[51] Int. Cl.$^5$ .................... C07C 46/06; C07C 50/04
[52] U.S. Cl. .................... 552/293; 552/295; 552/296; 552/308; 552/309
[58] Field of Search ............... 552/293, 308, 309, 295, 552/296

[56] References Cited

U.S. PATENT DOCUMENTS

| | | | |
|---|---|---|---|
| 1,987,148 | 1/1935 | Kleimenhagen | 552/293 |
| 4,235,790 | 11/1980 | Müller et al. | 552/293 |
| 4,420,036 | 4/1984 | Hsu et al. | 552/293 |
| 4,973,720 | 11/1990 | Saito et al. | 552/293 |

OTHER PUBLICATIONS

A. E. Gekhman et al, Kinet. Katal. 30, 362 (1989).
H. Firouzabadi and N. Iranpoor, Synthetic Communications 14, 875 (1984).
Makromol, Chem., Rapid Communication, 9, 705 (1988).
J. Mol. Catalysts 55, 379 (1989).
J. Pol. Sci. 15, 2059 (1977).
R. J. Radel et al, Ind. Eng. Chem. Prod. Res. Dev. 21, 566, (1982).
T. R. Demmin et al, J. Am. Chem. Soc. 103 5795 (1981).

Primary Examiner—Vivian Garner

[57] ABSTRACT

Disclosed is a process for the preparation of quinhydrones by the catalytic oxidation of aromatic diols with a peroxide in the presence of a catalyst system comprising a cerium carboxylate and a cupric carboxylate.

5 Claims, No Drawings

PROCESS FOR THE PREPARATION OF QUINHYDRONES

This invention pertains to the preparation of quinhydrones by the catalytic oxidation of aromatic diols. More specifically, this invention pertains to the preparation of quinhydrones by the oxidation of aromatic diols with a peroxide in the presence of a catalyst system comprising a cerium carboxylate and a cupric carboxylate.

As is described in Kirk-Othmer Encyclopedia of Chemical Technology, Third Edition, John Wiley and Sons, New York, 1981, pages 39–69, hydroquinone and p-benzoquinone form an equimolecular complex by charge transfer between the $\pi$ orbitals of the rings. This complex (quinhydrone) crystallizes to red brown needles that have a green surface shine ($T_m$ 171° C.).

Quinhydrone compounds are valuable chemicals which are useful as electron-donor-acceptor complexes in liquid crystal displays, as bactericides in the petroleum industry for inhibiting the growth of sulfate reducing bacteria, as components of sulfuric acid-based pickling solutions for steel, as components in oxidation-reduction electrodes, and as components in antifriction compositions based on polyethylene and powdered iron.

Quinhydrone compounds may be prepared by a variety of procedures. For example, quinhydrones may be prepared by mixing equimolar quantities of a hydroquinone and a quinone in a suitable solvent. The purity and utility of quinhydrone compounds made in this manner is highly dependent on the purity of the starting materials. Also for many substituted quinhydrone compounds, the necessary substituted hydroquinone and benzoquinone compounds are not always readily available.

The formation of quinhydrone by the oxidation of hydroquinone in the presence of a salt of trivalent cerium using oxygen or an oxygen containing gas is disclosed in A. E. Gekhman et al., Kinet. Katal. 30, 362 (1989). The use of a catalytic combination of a cerium carboxylate and a cupric carboxylate is not disclosed.

H. Firouzabadi and N. Iranpoor, Synthetic Communications 14, 875 (1984) describe the preparation of benzoquinone compounds by the oxidation of a benzene solution of benzenediols such as hydroquinone and catechol using ceric trihydroxyhydroperoxide [Ce(OH)$_3$OOH] as the oxidizing agent. This non catalytic process does not employ either air or a peroxide but uses two moles of the oxidizing agent per mole of the reactant.

There are many references in the literature to the use of copper compounds and copper complexes in the oxidation of phenolic compounds. The oxidation of hydroquinone with oxygen in the presence of a polyvinylpyridine-copper (II) complex and a poly(4-vinyl pyridine-co-N-vinylpyrrolidone) copper (II) complex is described by K. Yamashita et al., Polymer Bulletin 22, 728 (1989) and in Makromol, Chem., Rapid Communication, 9, 705 (1988). The use of copper (II) and cobalt (II)-polyvinylpyridine complexes in the oxidation of 3,5-di-t-butylcatechol with oxygen is disclosed in the J. Mol. Catalysis 55, 379 (1989). The oxidation of hydroquinone using oxygen in the presence of copper (II)-polyelectrolyte complexes is disclosed in J. Pol. Sci. 15, 2059 (1977). R. J. Radel et al., Ind. Eng. Chem. Prod. Res. Dev. 21, 566 (1982) describe the oxidation of hydroquinone with oxygen at both atmospheric and under pressure using various Cu (I) and Cu (II) salts, Ru/C, Pd/C, V$_2$O$_5$, Ru/Al$_2$O$_3$, and Rh/Al$_2$O$_3$ as catalysts. T. R. Demmin et al., J. Am. Chem. Soc. 103, 5795 (1981) describe the catalytic conversion of catechols to o-benzoquinones using oxygen in the presence of copper (II) salts.

We have discovered that quinhydrone compounds may be prepared in good yields by contacting an aromatic diol with a peroxide in the presence of an inert solvent and a catalyst system comprising a cerous (Ce$^{+++}$) carboxylate and a cupric carboxylate, wherein the peroxide:aromatic diol mole ratio is in the range of about 0.4 to 0.6. The use of other cerous salts has been found to give results substantially inferior to those which may be obtained in accordance with our invention. For example, ceric sulfate, cerous sulfate, cerium ammonium nitrate, cerium ammonium sulfate, cerous carbonate, and cerous nitrate are much less effective than cerous acetate.

The use of a cerous carboxylate in combination with a cupric carboxylate permits the use of a lower concentration of the more expensive cerous compound and also improves the filtration characteristics, e.g. filtration rates, of the reaction mixture. We have found that substantially inferior results are obtained when other metal salts such as cobalt acetate or manganese acetate are used as the cocatalyst instead of the cupric carboxylate compounds.

The aromatic diols which may be used in the process provided by the present invention include unsubstituted and substituted benzenediols, naphthalenediols, anthracenediols and the like. Examples of the substituents which may be presence on the substituted benzenediols and naphthalenediols include alkyl of up to about 12 carbon atoms, halogen such as chloro, cycloalkyl such as cyclohexyl and aryl such as phenyl. In addition to hydroquinone, specific examples of suitable aromatic diol reactants are 1,2-benzenediol, methyl 1,4-benzenediol, cyclohexyl-1,4-benzenediol, phenyl-1,4-benzenediol, 1,2- and 1,4-naphthalenediol, and the like. As used herein to describe the product of our novel process, "quinhydrone compound" refers to a complex consisting of substantially equimolar amounts of the aromatic diol reactant and its corresponding quinone compound. For example, the quinhydrone compound obtained from chlorohydroquinone consists of substantially equimolar amounts of chlorohydroquinone and chloro-p-benzoquinone.

A preferred group of benzenediol reactants have the general formula

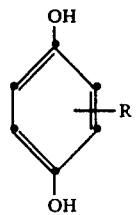

wherein R is hydrogen, alkyl of up to about 8 carbon atoms, halogen, cyclohexyl or phenyl.

Examples of the peroxides which may be used in our novel process include hydrogen peroxide; aliphatic peroxides such as alkyl peroxides, e.g., tertiary-butyl hydroperoxide; peracids such as percarboxylic acids i.e., a carboxylic acid peroxide, e.g., peracetic acid, perbutyric acid and perbenzoic acid; and the like. Hydrogen peroxide and peracetic acid are the preferred peroxides. The hydrogen peroxide suitable for use in the process comprises aqueous hydrogen peroxide having a peroxide content of 3 to about 90 weight percent. For economic and safety reasons, the aqueous hydrogen peroxide most suitable for use in the process has a hydrogen peroxide content of about 30 to 70 weight percent. It is well-known to those skilled in the art that peracetic acid may be generated in situ by several processes, the most important of which comprise the dissolution of hydrogen peroxide in acetic acid or acetic anhydride and the interaction of oxygen with acetaldehyde. These methods of in situ generation of the peroxide are within the scope of our invention. A particularly useful source of peracetic acid is the epoxidation process described by J. T. Lutz, Jr. in Kirk-Othmer, Encyclopedia of Chemical Technology, 3rd Ed., Vol. 9, p. 225-258 (1980). In the epoxidation process, peracetic acid is generated by contacting acetic acid with hydrogen peroxide in the presence of an acidic ion exchange resin.

The amount of peroxide employed in the process of the present invention can vary from 0.4 to 0.6 moles peroxide per mole of aromatic diol reactant. However, the best results are achieved by using about 0.48 to 0.52 moles peroxide per mole of diol reactant.

The cerous and cupric carboxylate catalyst components may be selected from cerous and cupric salts of various carboxylic acids, including dicarboxylic acids, such as cerous acetate, cupric acetate, cerous propionate, cupric propionate, cerous butyrate, cupric isobutyrate, cerous benzoate and the like. The combination of cerous and cupric carboxylates may be used in a mole ratio of cerous carboxylate:cupric carboxylate in the range of about 99:1 to about 10:90. However, to achieve the advantages provided by the present invention, the cerous carboxylate:cupric carboxylate mole ratio normally is within the range of about 80:20 to 40:60.

The catalytic amount of the cerium copper catalyst system can be varied substantially depending, for example, on the reaction conditions and the particular catalyst system employed. Thus, the total moles of cerous carboxylate and cupric carboxylate employed may be used in amounts ranging from about 0.01 to 1 mole of catalyst components (total moles of cerous and cupric carboxylate) per mole of aromatic diol reactant. The preferred catalyst system wherein the cerous carboxylate:cupric carboxylate mole ratio is within the range of about 80:20 to 40:60 preferably is employed in an amount which gives a catalyst:diol reactant mole ratio of about 0.04:1 to 0.1:1 . The catalyst system may be recovered and utilized in subsequent oxidations.

Our novel process is carried out in the presence of an inert solvent such as water, an aliphatic carboxylic acid such as acetic acid, mixtures of water and an aliphatic carboxylic acid and mixtures of an aliphatic carboxylic acid and a hydrocarbon such as benzene, toluene, hexane, heptane and the like. Normally, the amount of solvent employed gives a solvent:aromatic diol reactant weight ratio of about 5:1 to 20:1.

The process may be practiced at a temperature of about 0° to 80° C. although the use of temperatures in the upper portion of this range tends to cause some product degradation. The preferred temperature range is about 15° to 40° C. Reaction times of about 30 to 120 minutes normally give good results, e.g., quinhydrone product yields of about 60 to 98% based on the aromatic diol reactant. The quinhydrone product may be isolated according to conventional procedures such as by extraction, distillation, sublimation and the like.

The process of the present invention may be carried out in a batch, semi continuous or continuous manner. In continuous operation of the process, a solution of the diol reactant, a catalyst solution comprising fresh catalyst and recycle catalyst solution, and a peroxide may be fed to a reaction zone comprising one or more reactors maintained at the appropriate reaction temperature. The effluent from the reaction zone containing the quinhydrone product dispersed in the reaction mixture is fed to a product recovery zone wherein the product is separated, for example, by filtration using a rotary drum vacuum filtration apparatus. The filtrate containing catalyst components and any unconverted diol reactant is removed from the product recovery zone recycled to the reaction zone.

A particularly preferred embodiment of the process provided by the present invention concerns the preparation of quinhydrone by contacting a solution of hydroquinone and a cerous carboxylate/cupric carboxylate catalyst system in an inert solvent with aqueous hydrogen peroxide or peracetic acid at a temperature of about 15° to 40° C.

The operation of our novel process is further illustrated by the following examples wherein GLC refers to gas/liquid chromatography.

EXAMPLE 1

A 1000 mL, 3 neck flask fitted with a thermometer and an addition funnel is charged with 200 mL of water, 7.6 g (0.022 mole) of cerous acetate (1.5 hydrate), 4.5 g (0.022 mole) of cupric acetate, and 50 g (0.45 mole) of hydroquinone. The flask is immersed in a water bath to maintain the reaction mixture at a constant temperature. The solution is agitated with a mechanical stirrer at 25° C. for 5-10 minutes and then 25.75 g of 30% aqueous hydrogen peroxide (0.22 mole $H_2O_2$) is slowly added to the solution over a period of about 1 hour. The temperature of the solution first increases to about 30°-35° C. and then decreases to 25° C. and remains at that temperature throughout the reaction. The total reaction time is 2 hours. The quinhydrone product is collected by filtration and dried. The yield of quinhydrone is 47.15 g (94.1% of theory) having a melting point of 171° C. GLC analysis of a sample of the product dissolved in acetone confirms the presence of equimolar amounts of hydroquinone and p benzoquinone in the quinhydrone complex.

EXAMPLE 2

The procedure of Example 1 is repeated using 200 mL of water, 3.6 g (0.01 mole) of cerous acetate (1.5 hydrate), 2.3 g (0.01 mole) of cupric acetate monohydrate, 50 g (0.45 mole) of hydroquinone, and 25.75 g of 30% aqueous hydrogen peroxide (0.22 mole $H_2O_2$). The yield of quinhydrone is 88%.

EXAMPLE 3

The procedure of Example 1 is repeated using 200 mL of water, 3.2 g (0.009 mole) of cerous acetate (1.5 hydrate), 4.7 g (0.024 mole) of cupric acetate monohydrate, 50 g (0.45 mole) hydroquinone, and 25.75 g of 30% aqueous hydrogen peroxide (0.22 mole $H_2O_2$). The yield of quinhydrone is 70.3%.

EXAMPLE 4

The procedure of Example 1 is repeated using 200 mL of water, 7.5 g (0.022 mole) of cerous acetate (1.5 hydrate), 5.0 g (0.025 mole) of cupric acetate monohydrate, 75.0 g (0.68 mole) of hydroquinone and 38.64 g of 30% aqueous hydrogen peroxide (0.34 mole $H_2O_2$). The yield of quinhydrone is 93.8%.

EXAMPLE 5

Into a 50 mL, round bottom flask fitted with a dropping funnel and a magnetic stirrer are placed 40 mL of water, 2.0 g ($5.8 \times 10^{-3}$ mole) of cerous acetate, 0.75 g (0.0038 mole) of cupric acetate, and 2.9 g (0.02 mole) of chlorohydroquinone. A total of 1.13 g of 30% $H_2O_2$ (0.01 mole) is added dropwise to the reaction mixture with stirring and the reaction is continued at 25° C. for 1 hour. The solid quinhydrone product is collected by filtration and dried. The yield of quinhydrone product is 76%.

EXAMPLE 6

Into a 50 mL, round bottom flask fitted with a dropping funnel and a magnetic stirrer are placed 24 mL of water, 16 mL of acetic acid, 2.0 g (0.0058 mole) of cerous acetate, 0.75 g (0.0038 mole) of cupric acetate, and 3.3 g (0.02 mole) of tert butyl hydroquinone. A total of 2.1 g of 30% $H_2O_2$ (0.018 mole) is added dropwise to the reaction mixture with stirring and the reaction is continued at 25° C. for 1 hour. The quinhydrone product is collected by filtration and dried. The yield of quinhydrone product is 60%.

EXAMPLE 7

Into a 50 mL, round bottom flask fitted with a dropping funnel and a magnetic stirrer are placed 10 mL of water, 40 mL of acetic acid, 2.0 g (0.0058 mole) of cerous acetate, 0.75 g of (0.0038 mole) of cupric acetate, and 3.8 g (0.02 mole) of phenylhydroquinone. A total of 1.16 g of 30% aqueous hydrogen peroxide (0.01 mole $H_2O_2$), is added dropwise to the reaction mixture with stirring. The reaction is continued at 25° C. for 1 hour and the quinhydrone product is collected by filtration and dried. The yield of the quinhydrone product is 79%.

COMPARATIVE EXAMPLE 1

Into a 50 mL, round bottom flask fitted with a dropping funnel and a magnetic stirrer are placed 40 mL of $H_2O$, 1.6 g (0.005 mole) of cerous acetate, 1.25 g (0.005 mole) of cobalt acetate, and 4.4 g (0.04 mole) of hydroquinone. A total of 3.3 g of 30% aqueous hydrogen peroxide (0.029 mole $H_2O_2$) is added dropwise to the reaction mixture with stirring. The reaction is continued at 25° C. for 1 hour. The quinhydrone product then is separated by filtration and dried. The yield of the quinhydrone is 54%.

COMPARATIVE EXAMPLE 2

Into a 50 mL, round bottom flask fitted with a dropping funnel and a magnetic stirrer are placed 40 mL of $H_2O$, 1.6 g (0.005 mole) of cerous acetate, 1.23 g (0.005 mole) of manganese acetate, and 4.4 g (0.04 mole) of hydroquinone. A total of 3.3 g of 30% aqueous hydrogen peroxide (0.029 mole $H_2O_2$) is added dropwise to the reaction mixture with stirring and the reaction is continued at 25° C. for 1 hour. At the completion of the reaction, the reaction mixture is filtered to collect the solid quinhydrone product. The yield of the quinhydrone is found to be 45%.

The invention has been described in detail with particular reference to preferred embodiments thereof, but it will be understood that variations and modifications may be effected within the spirit and scope of the invention.

We claim:

1. Process for the preparation of a quinhydrone compound which comprises contacting an aromatic diol having the formula

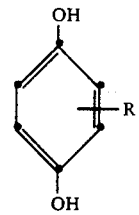

with a peroxide selected from hydrogen peroxide, alkyl peroxides and percarboxylic acids in the presence of a catalyst system comprising a cerous carboxylate and a cupric carboxylate and an inert solvent at a temperature of about 0° to 80° C., wherein the peroxide:aromatic diol mole ratio is in the range of about 0.4 to 0.6 and R is hydrogen, alkyl of up to about 8 carbon atoms, halogen, cyclohexyl or phenyl.

2. Process according to claim 1 wherein the aromatic diol is contacted with a peroxide selected from hydrogen peroxide and peracetic acid in the presence of an inert solvent and a catalyst system comprising a cerous carboxylate and a cupric carboxylate at a temperature of about 15° to 40° C. and wherein the cerous carboxylate:cupric carboxylate mole ratio is about 80:20 to 40:60 and the mole ratio of the catalyst system:aromatic diol is about 0.04:1 to 0.1:1.

3. Process for the preparation of a quinhydrone compound which comprises contacting an aromatic diol having the formula

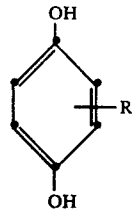

with a peroxide selected from hydrogen peroxide and peracetic acid in the presence of a catalyst system comprising a cerous carboxylate and a cupric carboxylate and an inert solvent at a temperature of about 15° to 40° C., wherein the cerous carboxylate:cupric carboxylate mole ratio is about 80:20 to 40:60, the mole ratio of the catalyst system to aromatic diol is about 0.04:1 to 0.1:1, the peroxide:aromatic diol mole ratio is in the range of about 0.4 to 0.6, and R is hydrogen, alkyl of up to about 8 carbon atoms, halogen, cyclohexyl or phenyl.

4. Process for the preparation of quinhydrone which comprises contacting a solution of hydroquinone and a catalyst system comprising a cerous carboxylate and a cupric carboxylate in an inert solvent with aqueous hydrogen peroxide or peracetic acid at a temperature of about 15° to 40° C. wherein the peroxide:hydroquinone mole ratio is in the range of about 0.4 to 0.6.

5. Process according to claim 4 for the preparation of quinhydrone which comprises contacting a solution of hydroquinone and a catalyst system comprising cerous acetate and a cupric acetate in an inert solvent selected from water, acetic acid or a mixture thereof with aqueous hydrogen peroxide or peracetic acid at a temperature of about 15° to 40° C., wherein the cerous carboxylate:cupric carboxylate mole ratio is about 80:20 to 40:60 and the mole ratio of the catalyst system:hydroquinone is about 0.04:1 to 0.1:1.

* * * * *